US009186474B1

(12) United States Patent
Rollins, III

(10) Patent No.: US 9,186,474 B1
(45) Date of Patent: Nov. 17, 2015

(54) MULTI-FUNCTION OXYGEN MASK

(75) Inventor: Offord L. Rollins, III, Las Vegas, NV (US)

(73) Assignee: ROLLINS MEDICAL SOLUTIONS, INC., Las Vegas, NV (US)

(*) Notice: Subject to any disclaimer, the term of this patent is extended or adjusted under 35 U.S.C. 154(b) by 147 days.

(21) Appl. No.: 13/081,457

(22) Filed: Apr. 6, 2011

Related U.S. Application Data

(60) Provisional application No. 61/321,188, filed on Apr. 6, 2010.

(51) Int. Cl.
*A61M 16/06* (2006.01)
*A61M 16/14* (2006.01)

(52) U.S. Cl.
CPC .............. *A61M 16/06* (2013.01); *A61M 16/14* (2013.01)

(58) Field of Classification Search
CPC ............ A61M 16/06; A61M 16/0683; A61M 16/0816; A61M 16/0875; A61M 16/20; A61M 16/0003; A61M 16/208; A61M 16/0833; A61M 2016/0661; A61M 16/08; A61M 16/0858; A61M 2202/0208; A61M 16/007; A61M 16/00; A61M 16/0057; A61M 16/0078; A61M 16/0081; A61M 16/0488; A61M 16/049; A61M 16/0493; A61M 16/0495; A61M 16/0497; A61M 16/0605; A61M 16/0611; A61M 16/0616; A61M 16/0622; A61M 16/14; A62B 18/02; A62B 18/025; A62B 18/06
See application file for complete search history.

(56) References Cited

U.S. PATENT DOCUMENTS

| 4,328,797 | A  | * | 5/1982  | Rollins et al. | 128/202.27 |
|-----------|----|---|---------|----------------|------------|
| 6,578,571 | B1 | * | 6/2003  | Watt           | 128/200.14 |
| 8,042,540 | B2 |   | 10/2011 | McDonald et al.|            |
| 2003/0024533 | A1 | * | 2/2003 | Sniadach | 128/205.25 |
| 2006/0196510 | A1 | * | 9/2006 | McDonald et al. | 128/206.21 |
| 2007/0012360 | A1 | * | 1/2007 | Flynn | 137/102 |
| 2008/0000472 | A1 | * | 1/2008 | Wall | 128/202.27 |
| 2008/0210242 | A1 | * | 9/2008 | Burk et al. | 128/206.21 |
| 2008/0230072 | A1 | * | 9/2008 | Rollins et al. | 128/207.15 |
| 2009/0260628 | A1 | * | 10/2009 | Flynn, Sr. | 128/203.28 |

* cited by examiner

*Primary Examiner* — Loan H Thanh
*Assistant Examiner* — Andrew S Lo
(74) *Attorney, Agent, or Firm* — Todd J. Langford; Eric A. Hanscom

(57) ABSTRACT

A multi-function oxygen mask is disclosed which generally comprises a mask body and a gas delivery adapter. The mask body forms an internal cavity configured to cover a nose and mouth of a patient. A nasal chamber is formed in the upper portion of the mask body, the nasal chamber includes an upper portion, a lower portion and a gas delivery adapter aperture adjacent the lower portion of the nasal chamber. An access aperture is formed through and adjacent to the lower portion of the mask body. The access aperture is configured to permit access to the mouth of a patient. The gas delivery adapter has a general tubular structure and includes a first end an opposing second end, the first end of the gas delivery adapter is coupled to the gas delivery adapter aperture. An oxygen supply port radially extends outward from the gas delivery adapter and adjacent to the first end of the gas delivery adapter. The oxygen supply port further includes an external inlet portion, an outlet portion positioned within a volumetric space of the gas delivery adapter and a diverter member adjacent to the outlet portion. The diverter member is configured to direct a flow towards the first end of the gas delivery adapter. A meter-dose inhaler port radially extends outward from the gas delivery adapter. Finally, the gas delivery adapter includes a meter-dose inhaler port and a nebulizer port.

16 Claims, 5 Drawing Sheets

MULTI-FUNCTION OXYGEN MASK

CROSS-REFERENCE TO RELATED APPLICATIONS

This Non-Provisional Utility Patent Application claims priority to U.S. Provisional Patent Application Ser. No. 61/321,188 filed on Apr. 6, 2010, which is incorporated herein in its entirety.

FIELD OF THE INVENTION

The present disclosure generally relates to oxygen delivery masks. More particularly, the present disclosure relates to an improved multi-function oxygen mask, which facilitates multiple respiratory treatments of a patient.

BACKGROUND OF THE INVENTION

Currently, a wide variety of oxygen masks are commercially available, varying in construction, style, and material, depending upon the specific use or procedure employed. The basic oxygen mask that is available today uses neither a valve nor a reservoir bag. Exhaled air from the lungs of the patient is usually vented through holes in the body of the mask. In view of its convenience and relative comfort, the basic oxygen mask is frequently used whenever moderate oxygen concentrations are desired for short periods of time. This might occur, for example, during the postoperative recovery state of a patient. Such a mask might also be used, for example, during either temporary or interim respiratory therapy when a patient is being weaned from continuous oxygen administration.

In many postoperative states and various medical cases, a patient may require multiple treatments while simultaneously receiving oxygen therapy. For example a patient may need a naso-gastric tube, suctioning, oral care, nebulizer treatment, endoscopies, cooled/headed aerosol mist, aerosol delivered medication (Meter-Dose Inhaler "MDI") or combinations thereof. In the past, a medical provider typically would have to use a specialty mask specifically designed for the medical treatment being delivered to the patient. While this approach is somewhat effective, it presents several substantial drawbacks. Firstly, this approach requires the provider to inventory several different types of oxygen masks resulting in increased overhead costs. Secondly, in the situation where the patient requires multiple types of treatments, the patient will likely have multiple masks at their bedside, which is psychologically intimidating. Thirdly, a patient may have an emergency requirement for a specific treatment and the time spent locating and acquiring the specific type of oxygen mask may compromise the medical condition/treatment of the patient. Fourthly, the patient may have difficulty communicating, eating or drinking, while maintaining proper oxygen concentration, because known oxygen masks frequently have to be removed prior to these activities. Finally, oxygen masks currently available, including specialty masks, have difficulty in supplying high oxygen concentrations at low volumetric flow rates.

The standard oxygen mask used to provide oxygen treatment to a patient is one known device, while somewhat useful, presents substantial drawbacks. This type of oxygen mask is generally a single-purpose mask and provides very limited functionality. This known device is generally devoid of provisions for nebulizer treatments, aerosol administered medications (MDI), naso-gastric tube placement, cooled/heated aerosol misting, patient comfort/communication or combinations thereof. Further, these known devices frequently underperform when high oxygen concentrations at low volumetric flow rates are required.

Another known solution is an oxygen venturi mask with nebulizer capability. This known solution, while somewhat useful, presents substantial drawbacks. This type of oxygen mask is generally a specialty mask and provides very limited functionality. This known device is generally devoid of provisions for aerosol administered medications (MDI), naso-gastric tube placement, suctioning, endoscopies, oral care, eating/drinking, patient comfort/communication or combinations thereof. Further, this known device frequently underperforms when high oxygen concentrations at low volumetric flow rates are required.

Also known, is an oxygen aerosol mask with nebulizer that facilitates nebulizer and aerosol misting treatments. This known solution, while somewhat useful, presents substantial drawbacks. This type of oxygen mask is generally a specialty mask and provides very limited functionality. This known device is generally devoid of provisions for aerosol administered medications (MDI), naso-gastric tube placement, suctioning, endoscopies, oral care, eating/drinking, patient comfort/communication or combinations thereof. Further, this known device frequently underperforms when high oxygen concentrations at low volumetric flow rates are required.

A partial oxygen non-rebreather mask with nebulizer is another known solution and while somewhat useful, presents substantial drawbacks. This type of oxygen mask is generally a specialty mask and provides very limited functionality. This known device is generally devoid of provisions for naso-gastric tube placement, suctioning, endoscopies, oral care, eating/drinking, patient comfort/communication or combinations thereof. Additionally, this type of oxygen mask is generally a large device that covers a significant portion of the face of a patient and increases the feeling of claustrophobia. Further, this known device frequently underperforms when high oxygen concentrations at low volumetric flow rates are required Efforts to provide a multi-function oxygen mask that overcomes the drawbacks in the prior art have not met with significant success to date. As a result, there is a need in the art for an oxygen mask that provides increased functionality with multiple medical treatments, increases patient comfort and reduces supply inventory/expenditures.

SUMMARY OF THE INVENTION

The basic inventive concept provides a multi-function oxygen mask that permits the administration of multiple medical procedures without interrupting oxygen supply to a patient, increases patient comfort and reduces costs associated with proving medical services.

From an apparatus aspect, the invention comprises a multi-function oxygen mask for the administration of a gas such as oxygen. The oxygen mask generally comprises a mask body and a gas delivery adapter. The mask body forms an internal cavity configured to cover a nose and mouth of a patient. Included in the mask body are an upper portion, a lower portion, a peripheral edge, a sealing edge laterally extending outward from the peripheral edge, and an upper sealing edge formed adjacent to the upper portion of the mask body. A nasal chamber is formed in the upper portion of the mask body. The nasal chamber includes an upper portion, a lower portion and a gas delivery adapter aperture adjacent the lower portion of the nasal chamber. An access aperture is formed through and adjacent to the lower portion of the mask body, the access aperture is configured to permit access to the mouth of a patient.

The gas delivery adapter has a general tubular structure and includes a first end an opposing second end, the first end of the gas delivery adapter is coupled to the gas delivery adapter aperture. An oxygen supply port radially extends outward from the gas delivery adapter and adjacent to the first end of the gas delivery adapter. The oxygen supply port further includes an external inlet portion, an outlet portion positioned within a volumetric space of the gas delivery adapter and a diverter member adjacent to the outlet portion. The diverter member is configured to direct a flow towards the first end of the gas delivery adapter. A meter-dose inhaler port radially extends outward from the gas delivery adapter. Finally, a nebulizer port extends longitudinally from the second end of the gas delivery adapter.

In alternate apparatus embodiments, the invention further comprises a meter-dose inhaler insert within the meter-dose inhaler port, the meter-dose inhaler insert having a discharge port positioned within the volumetric space and configured to direct a flow towards the first end of the gas delivery adapter. In another embodiment, there is provided an oxygen supply port cover and a nebulizer port cover for sealing these ports when not in use. In yet another embodiment upper sealing edge forms an angle β (Beta) with respect to a sealing surface such that a central inflection point is positioned substantially at a midpoint of a bridge of the nose of the patient, wherein the angle β (Beta) is between about 30 and about 75 degrees. Additionally, upper sealing edge includes a right side and a left side that are each curved such that the upper portion of the mask body conforms to a facial structure of the patient. At least one naso-gastric tube aperture may be formed through the mask body and adjacent to the sealing edge From a method aspect, the invention comprises a method of fabricating a multi-function oxygen mask comprising the steps of: a) forming a mask body having an internal cavity configured to cover a nose and mouth of a patient, the mask body including an upper portion, a lower portion, a peripheral edge, a nasal chamber having an upper portion and a lower portion, an access aperture adjacent to the lower portion of the mask body, an upper sealing edge adjacent to the upper portion of the mask body and a gas delivery adapter aperture adjacent to the lower portion of the nasal chamber; b) coupling a first end of a gas delivery adapter to the gas delivery adapter aperture; c) providing an oxygen supply port adjacent to first end of the gas delivery adapter, the oxygen supply port having an inlet portion, an outlet portion positioned within a volumetric space of the gas delivery adapter; and d) providing a diverter member adjacent to the outlet portion, the diverter member configured to direct a flow towards the first end of the gas delivery adapter.

In alternate method embodiments, the invention further comprises various steps such as: inserting a meter-dose inhaler insert within the meter-dose inhaler port, the meter-dose inhaler insert having a discharge port positioned within the volumetric space and configured to direct a flow towards the first end of the gas delivery adapter; providing an oxygen supply port cover and a nebulizer port cover configured to seal these ports when not in use; forming an angled upper sealing edge such that a central inflection point is positioned substantially at a midpoint of a bridge of the nose of the a patient; forming a curved upper sealing such that the upper portion of the mask body conforms to a facial structure of the patient.

For a fuller understanding of the nature and advantages of the present invention, reference should be made to the ensuing detailed description of the preferred embodiments taken in conjunction with the accompanying.

BRIEF DESCRIPTION OF THE DRAWINGS

The components in the figures are not necessarily to scale, emphasis instead being placed upon illustrating the principles of the invention. The invention will now be described, by way of example, with reference to the accompanying drawings, in which.

In the figures, like reference numerals designate corresponding elements throughout the different views of the drawings.

DETAILED DESCRIPTION OF THE PREFERRED EMBODIMENTS

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. In other implementations, well-known features and methods have not been described in detail so as not to obscure the invention. For purposes of description herein, the terms "upper," "lower," "left," "right," "front," "back," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments, which may be disclosed herein are not to be considered as limiting, unless the claims expressly state otherwise.

Figure 1:
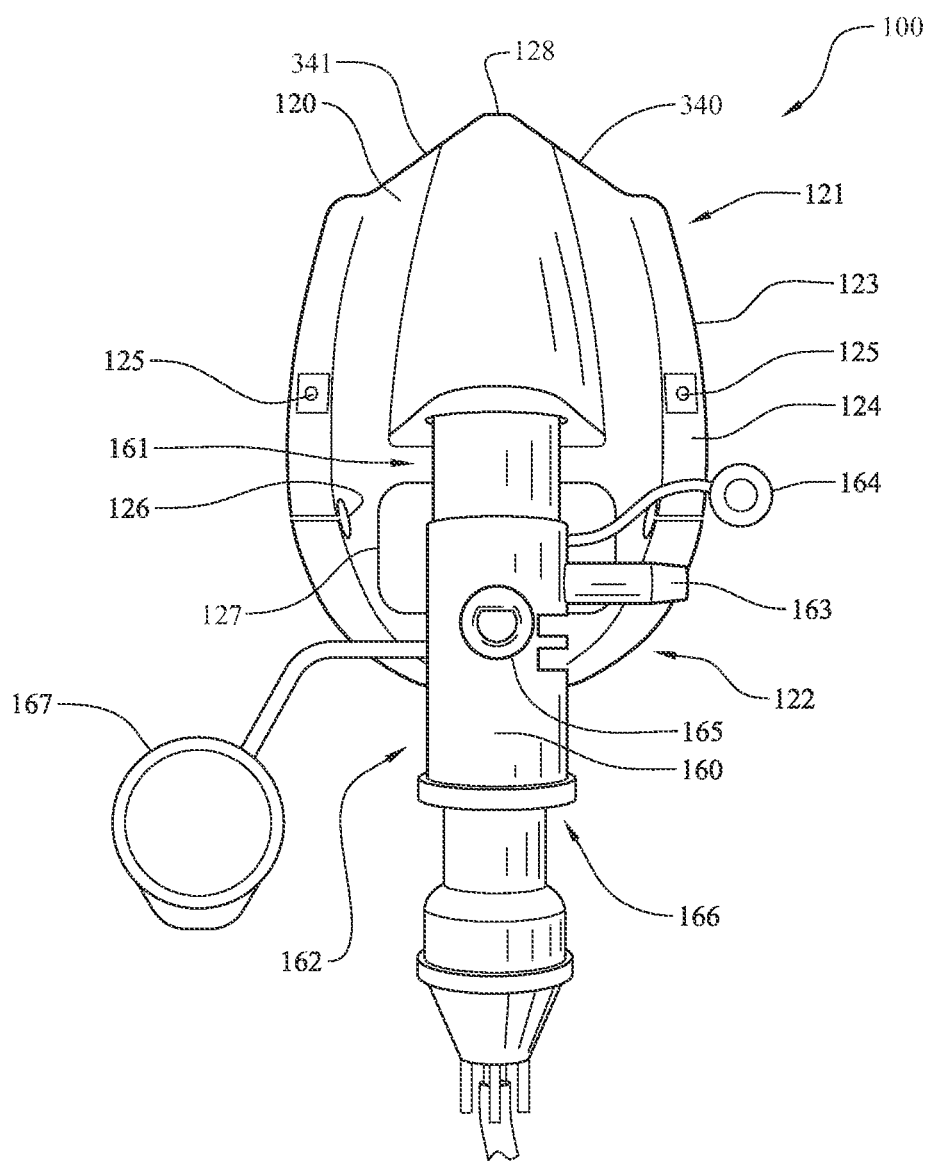
FIG. 1 is a elevation view of an exemplary embodiment of a multi-function oxygen mask in accordance with the present invention.
Figure 2:
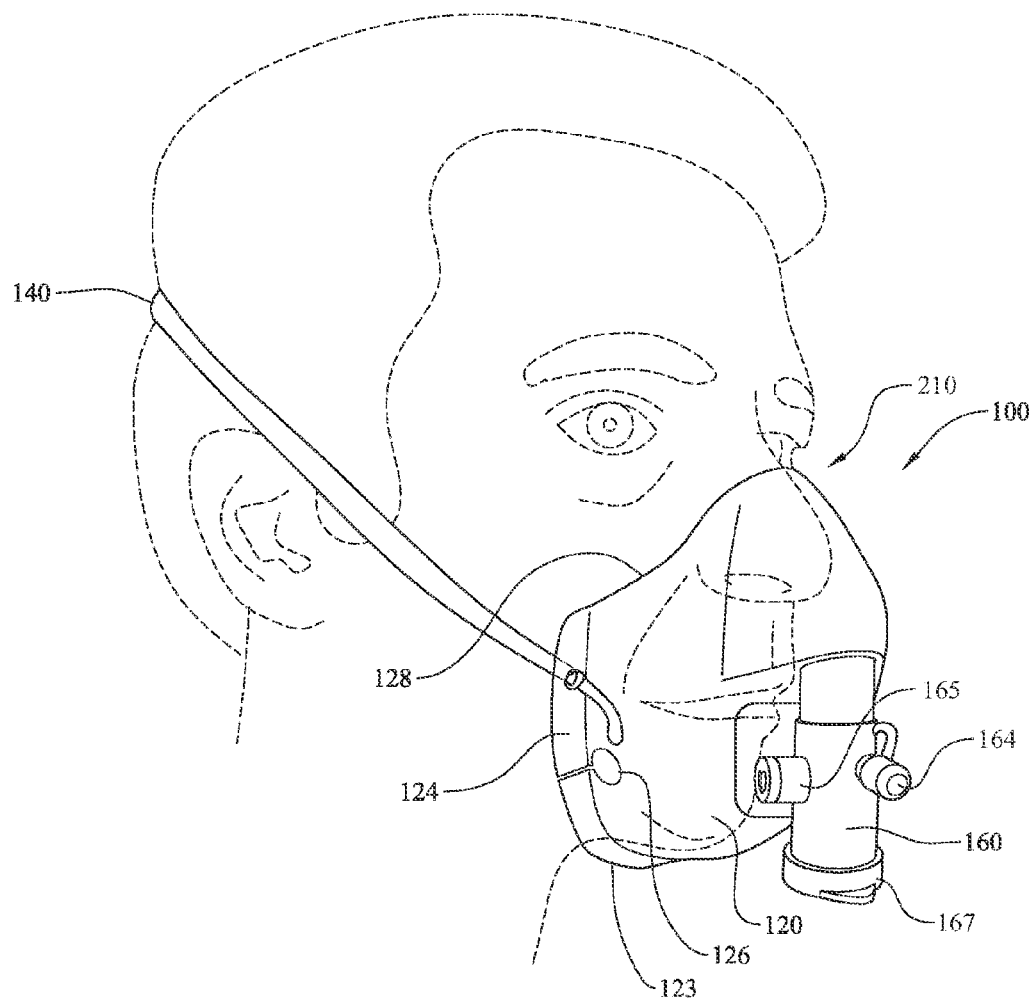
FIG. 2 is an isometric view of the multi-function oxygen mask on an individual in accordance with the present invention.

Reference is now made to FIGS. 1 and 2, which show a multi-function oxygen mask 100 that comprises a mask body 120, retention strap 140 and a gas delivery adapter 160. The mask body 120 forms an internal cavity that covers the nose and mouth of patient such that the patient inhales/exhales into the internal cavity when the mask 100 is placed on the patient. The gas delivery adapter 160 provides multiple ports through which various gases, medicines and treatments may be administered to a patient. Mask body 120 includes an upper portion 121, a lower portion 122, a peripheral edge 123, a sealing surface 124, a pair of securing strap holes 125, one or more naso-gastric tube apertures 126, an access aperture 127 and an upper sealing edge 128. Mask body 120 is preferably configured such that upper sealing edge 128 is relatively positioned adjacent to a midpoint 210 on the bridge of the nose of the patient as shown in FIG. 2. Gas delivery adapter 160 includes a first end 161, a second end 162, an oxygen supply port 163, an oxygen supply port cover 164, a meter-dose inhaler (MDI) port 165, a nebulizer port 166 and a nebulizer port cover 167. Mask body 120 is preferably fabricated from a transparent, thin, pliable plastic material that readily conforms to the facial structure of a patient. Gas delivery adapter 160 may be fabricated from many well-known materials such as plastics, composites and the like. One of ordinary skill in the art would readily understand these materials and the various manufacturing processes (e.g., injection molding, thermal forming etc) that may be employed to produce the multi-function oxygen mask 100 of the present invention. These materials and processes are not described in detail herein so as not to obscure the invention.

Figure 3:
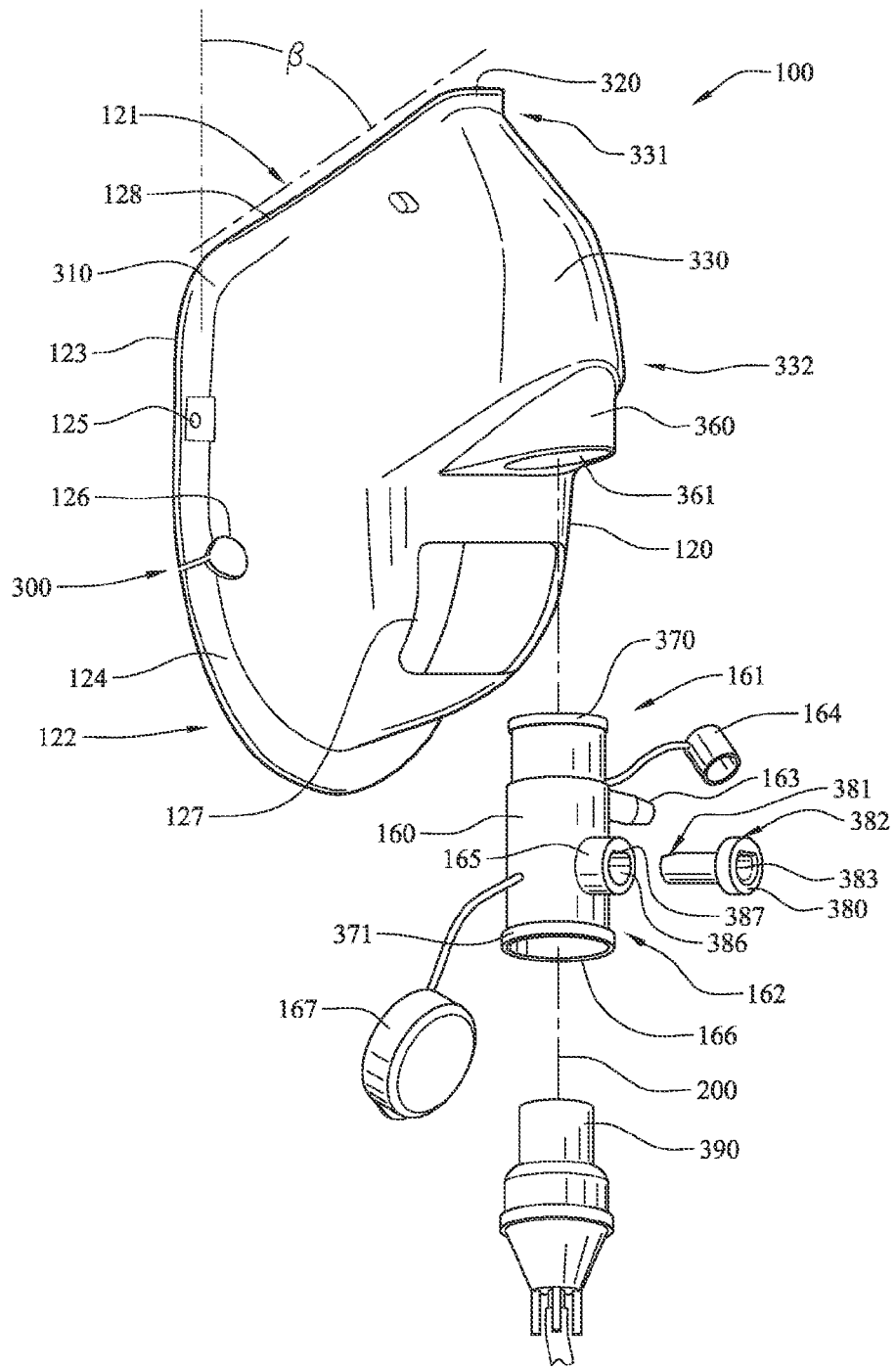
FIG. 3 is an exploded isometric view of the multi-function oxygen mask in accordance with the present invention.

Attention is now directed towards FIG. 3, which illustrates an exploded isometric view of the multi-function oxygen mask 100 including the mask body 120 and the gas delivery adapter 160 in accordance with the present invention. In one exemplary embodiment, mask body 120 includes an upper portion 121, a lower portion 122, a peripheral edge 123, a sealing surface 124, a pair of securing strap holes 125, one or more naso-gastric tube apertures 126, an access aperture 127 and an upper sealing edge 128. Sealing surface 124 laterally extends from peripheral edge 123 and generally conforms to the facial structures of a patient such that the flow of gases or oxygen in or out of the internal cavity is permitted through predefined passages. Securing strap holes 125 are formed within sealing surface 124 and when combined with a retention strap 140, provide a means for securing the multi-function oxygen mask 100 to a patient. Securing strap holes 125 are configured to releasably retain an elastomeric retention strap 140 such that the tension of the strap 140 may be adjusted according to patient comfort and positional requirements. It is contemplated that other types and configurations regarding the retention strap 140 may be employed such as retention clips, pins, slots or combinations thereof to provide a means for coupling the retention strap 140 to the mask body 120. Additionally, one or more naso-gastric tube apertures 126 may be formed through the mask body 120 and adjacent to sealing surface 124 such that a naso-gastric tube may pass there through. Although naso-gastric tube apertures 126 are illustrated in a generally circular shape other geometric profiles may be employed and will be readily understood by those of ordinary skill in the art. Further, a relief cut 300 may be provided through sealing surface 124 and into an adjacent naso-gastric aperture 126 wherein a naso-gastric tube can be routed into and out of the mask body 120 without having to remove the naso-gastric tube from the patient. To enhance the sealing capability of sealing surface 124, relief cut 300 may be a semi-perforated seam that can be opened when required for use.

In an exemplary embodiment, an access aperture 127 is formed through and adjacent to the lower portion 122 of mask body 120. Access aperture 127 is preferably positioned such that it is adjacent to the mouth and chin of a patient when the multi-function oxygen mask 100 is placed on a patient. Although access aperture 127 is illustrated in a generally rectangular shape other geometric profiles may be employed and will be readily understood by those of ordinary skill in the art. Access aperture 127 is symmetrically located about a centerline 200 of mask body 120 and sized to dimensionally maximize the open area to thereby facilitate access to the mouth of a patient.

Continuing with this exemplary embodiment, an upper sealing edge 128 is formed in mask body 120 and adjacent to upper portion 121. Upper sealing edge 128 generally extends from a laterally positioned inflection point 310 towards a central inflection point 320. Lateral inflection point 310 may be generally defined as a point along sealing surface 124 located lateral of the mask body 120 centerline 200 and adjacent to the upper portion 121. Central inflection point 320 may be generally defined as a point located at an apex of the upper most portion of mask body 120. Mask body 120 further comprises a nasal chamber 300 that substantially covers and conforms to the nose of a patient. Nasal chamber 330 includes an upper portion 331 and a lower portion 332. For dimensional relation, it is preferential that the mask body 120 be configured such that the upper portion 331 is positioned adjacent to a midpoint 210 of the bridge of the nose of a patient and the lower portion 332 is positioned adjacent to a tip of the nose of a patient. In one exemplary embodiment, the distance between upper portion 331 and lower portion 332 is minimized to about 1" to 3". It is contemplated that central inflection point 320 be located substantially adjacent to upper portion 331 of nasal chamber 330. Further, the upper sealing edge 128 is symmetrical with respect to a centerline 200 of mask body 120 resulting in a right side upper sealing edge 340 and left side upper sealing edge 341, as viewed from the front (see FIG. 1). Consequently, each side 340 and 341 of upper sealing edge 128 forms an angle β (Beta) with sealing surface 124 wherein angle β (Beta) may be about 30 to about 75 degrees. In one exemplary embodiment, the sides 340 and 341 of upper sealing edge 128 may be configured in a curved shaped to facilitate conformity with the facial structure of the patient. Alternatively, the sides 340 and 341 of upper sealing edge 128 may be generally linear.

Located below lower portion 332 of nasal chamber is a gas delivery adapter port 360, which includes an adapter aperture 361 that is configured and sized to accept the first end 161 of gas delivery adapter 160 therein. In this exemplary embodiment, the inside diameter of gas delivery adapter aperture 361 is sized to fit around the outside diameter of first end 161 of gas delivery adapter 160 such that adapter 160 may rotate about axis/centerline 200. Gas delivery adapter 160 is removably retained within gas delivery adapter port 360 by retention flange 370 that is formed on a distal edge of upper portion 161. The outside diameter of retention flange 370 is greater than the inside diameter of adapter aperture 361 such that when the gas delivery adapter 160 is inserted, the pliant mask material stretches and permits a press fit of the first end 161 into adapter aperture 361.

Interest is now directed towards the gas delivery adapter 160 illustrated in FIG. 3, where gas delivery adapter 160 includes a first end 161, a second end 162, an oxygen supply port 163, an oxygen supply port cover 164, a meter-dose inhaler (MDI) port 165, an MDI insert 380, a nebulizer port 166 and a nebulizer port cover 167. The gas delivery adapter 160 is generally a tubular structure that has an oxygen supply port 163 radially extending outward therefrom. The oxygen supply port 163 is sized and configured to receive and support a gas/oxygen supply hose thereon and is discussed in greater detail with reference to FIG. 6. There is also provided an oxygen supply port cover 164 which is flexibly formed from the gas delivery adapter 160 and is sized and configured for releasable coupling to the oxygen supply port 163 to effectively seal port 163 when not in use. In this exemplary embodiment there is provided an MDI port 165 that is located adjacent to the oxygen supply port 163 and radially extends outward from the gas delivery adapter 160. MDI port 165 is generally a tubular boss that has an insert aperture 386 that is keyed such that MDI insert 380 cannot rotate once inserted therein. Insert aperture 386 may be keyed by using a flat surface 387 that has a corresponding surface on MDI insert 380. However, other structural configurations are contemplated that provide registration and prohibit rotation of the MDI insert 380 within insert aperture 386 such as: multi-sided surfaces, spline surfaces, ridges, keyways etc.

In this embodiment, MDI insert 380 comprises a first end 381 and a second end 382. First end 381 is sized and configured for a press-fit engagement with insert aperture 386 and second end 382 is sized and configured to receive a portion of a discharge tube of a meter-dose inhaler (not shown) therein. Gas delivery adapter 160 further includes a nebulizer port 166 adjacent to the second end of the gas delivery adapter 160. The nebulizer port has an inner diameter that corresponds to and is configured for releasable retention of an outer diameter of a nebulizer 390. Alternatively, nebulizer port 166 may be coupled with the corrugated tubing of a humidifier (not shown). It is contemplated that the outside diameter of nebulizer port 166 be sized and configured to accept a portion of the corrugated tubing thereon. When not in use, nebulizer port 166 may be sealed by coupling nebulizer port cover 167 thereto. Cover 167 is held in place by retention flange 371.

Figure 4:
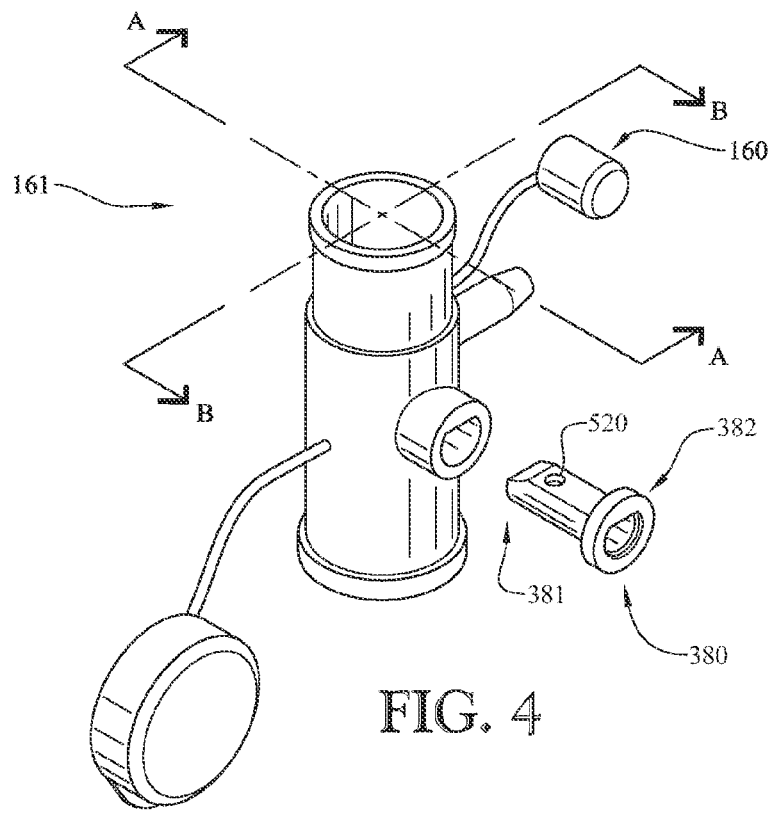
FIG. 4 is an isometric view of the gas delivery adapter of the multi-function oxygen mask in accordance with the present invention and illustrating section line A-A and section line B-B.
Figure 5:
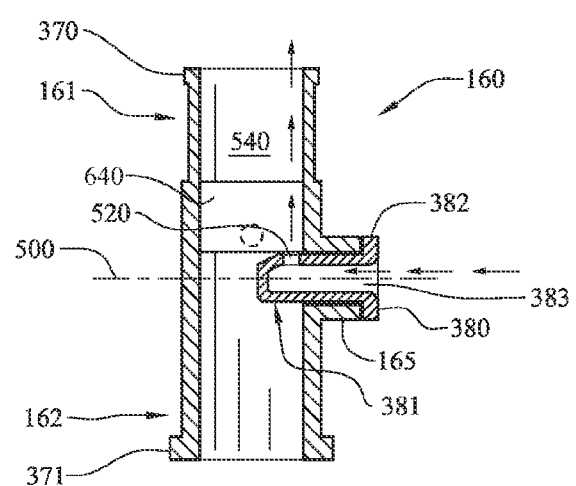
FIG. 5 is a section view of the gas delivery adapter taken along section line A-A of FIG. 4.

In an exemplary embodiment, and referring to FIGS. 4 and 5, the gas delivery adapter 160 includes an MDI port 165 and an MDI insert 380 inserted therein. Alternatively, MDI port 165 and MDI insert 380 may be formed as a one-piece unitary structure. MDI insert 380 comprises an inner passage 383 that is sized and configured to accept a portion of a discharge tube of a meter-dose inhaler (not shown). For example, inner passage 383 may be tapered such that only a portion of the discharge tube is permitted to be inserted therein. As a result, when the discharge tube of the meter-dose inhaler is inserted into inner passage 383 there is sufficient resistance and opposing force to actuate a discharge valve of the meter-dose inhaler. Also, the distal first end 381 of MDI insert 380 is closed with respect to the central axis 500 thereof. The first end 381 of MDI insert 380 comprises a discharge port 520 that directs flow within the inner passage 383 towards the first end 161 of the gas delivery adapter 160 as indicated by the flow lines in FIG. 5. Discharge port 520 is positioned within an interior volumetric space 540 of gas delivery adapter 160. In one exemplary embodiment, discharge port 520 is configured to discharge flow in a direction that is substantially perpendicular to central axis 500 and oriented towards the first end 161 of the gas delivery adapter 160.

Figure 6:
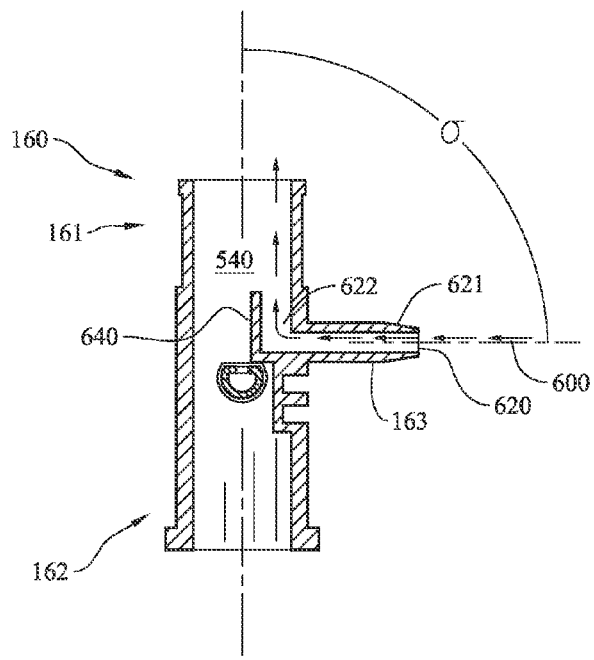
FIG. 6 is a section view of the gas delivery adapter taken along section line B-B of FIG. 4.

Now turning to FIGS. 4 and 6, in combination, the gas delivery adapter 160 includes an oxygen supply port 163 having a central axis 600 and an inner passage 620 formed therein. Inner passage 620 includes an external inlet portion 621 and an outlet portion 622 positioned within the interior volumetric region 540 of gas delivery adapter 160. Located adjacent to outlet portion 622 is a diverter member 640 that functions to direct flow within the inner passage 620 towards the first end 161 of the gas delivery adapter 160, as indicated by the flow lines in FIG. 6. Diverter member 640 is integrally formed within the gas delivery adapter 160 and extends from an inner surface towards the center and then extends towards the first end 161 of the gas delivery adapter 160. Generally, diverter member 640 forms an L-shaped flange below and adjacent to the outlet portion 622 and extends towards the first end 161 such that a channel/pocket is formed within the volumetric region 540 of gas delivery adapter 160. In one exemplary embodiment, diverter member 640 is configured to discharge flow in a direction that is substantially perpendicular to central axis 600 and oriented towards the first end 161 of the gas delivery adapter 160. It is contemplated that oxygen supply port 163 is positioned adjacent to the first end 161 of the gas delivery adapter 160. In an alternate embodiment, an angle θ (Theta) formed between central axis 600 of oxygen supply port 163 and central axis 660 of the first end 161 of gas delivery adapter 160 may be greater than 90 degrees. For example, angle θ (Theta) may be between about 90 and about 160 degrees.

Figure 7:
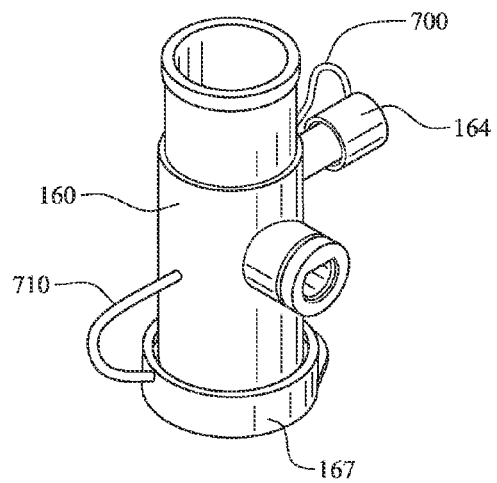
FIG. 7 is an isometric view of the gas delivery adapter of the multi-function oxygen mask in accordance with the present invention and illustrating two port covers in place.

Port covers 164 and 167 are illustrated in FIG. 7. Oxygen supply port cover 164 is flexibly coupled with gas delivery adapter 160 by way of retention member 700. Nebulizer port cover 167 is likewise flexibly coupled with gas delivery adapter 160 by way of retention member 710. Retention members 700 and 710 may be integral fabricated from gas delivery adapter 160 and preferably configured to flex without fracturing. Port covers 164 and 167 are employed when one or more ports are not being used. It is also contemplated that an MDI cover (not shown) may be provided to seal MDI port 165 when not in use.

In one exemplary embodiment, central axis 500 of MDI port 165 and central axis 600 of oxygen supply port 163 are oriented substantially perpendicular to one another. In an alternate embodiment, central axis 500 and central axis 600 may be oriented substantially parallel. Additionally, in yet another alternative embodiment, central axis 500 and central axis may be co-axially aligned. It is further contemplated, in an alternative embodiment, that MDI port 165 may extend from oxygen supply port 163. In this embodiment, discharge port 520 is preferably configured to direct flow substantially aligned with flow within the oxygen supply port.

In operation, and referring to FIGS. 1 through 7, a first step in utilizing the multi-function oxygen mask 100 of the present invention involves connecting an oxygen supply hose to the oxygen supply port 163. The second step involves setting the desired oxygen flow rate through the supply hose. Next, the multi-function oxygen mask 100 is placed over the nose and mouth of a patient and secured in place with retention strap 140. In further operation, aerosol medication may be administered by inserting a discharge tube of a meter-dose inhaler into the inner passage 383 of the MDI port 165 and actuating the discharge valve of the meter-dose inhaler. In the event that a nebulizer treatment required, nebulizer port cover 167 is removed from the nebulizer port 166. A nebulizer 390 is coupled to port 166 and the nebulizer treatment proceeds according to standard procedures.

During operation, it has been tested that the following concentrations at volumetric flow rates are possible:

| Oxygen Concentration | Volumetric Flow Rate |
| --- | --- |
| 28-33% | 2 L/min |
| 34-47% | 3 L/min |
| 48-53% | 4 L/min |
| 54-69% | 5 L/min |
| 70-75% | 6 L/min |
| 76-86% | 8 L/min |

| Oxygen Concentration | Volumetric Flow Rate |
|---|---|
| 87-95% | 10 L/min |
| 95-99% | ≥15 L/min |

As will be now apparent to those skilled in the art, multi-function oxygen masks fabricated according to the teachings of the present invention are capable of substantially facilitating the administration of multiple respiratory therapies and medical treatments. Since the present invention permits the patient to receive additional medical treatment without disrupting the basic oxygen therapy the device enhances and facilitates the medical treatment of the patient. In addition, the invention provides a device and method of use that greatly reduces the number of different/specialty oxygen masks than need to be purchased, stored and inventoried. Importantly, the present invention provides a multi-function oxygen mask that permits delivery of high concentration oxygen at low, medium and high volumetric flow rates. Further, the present invention provides a device that permits secondary procedures such as suctioning, oral care, feeding, endoscopies etc. to be administered without removal of the oxygen mask nor disruption of oxygen therapy. Specifically, with the present invention, it is possible to administer nebulizer/MDI treatment concurrently with high flow oxygen therapy. Additionally, the present invention substantially reduces carbon-dioxide retention in a patient receiving oxygen treatment. Finally, the invention provides a device that minimizes the covered surface area of the face of a patient, which in turn increases patient comfort (i.e., feeding, drinking, wearing glasses etc.) and alleviates the potential for claustrophobia.

Although the above provides a full and complete disclosure of the preferred embodiments of the invention, various modifications, combinations, alternate constructions and equivalents will occur to those skilled in the art. For example, although the invention has been described with reference to releasably coupling the mask body and the gas delivery adapter, alternatively these components may be permanently coupled or integrally formed together. In addition, although the MDI port has been described as extending outward and perpendicular to a central axis other configurations are possible such as extending angularly or co-axially therefrom. It is intended that all matters in the foregoing description and shown in the accompanying drawings be interpreted as illustrative and not in a limiting sense. Therefore the above should not be construed as limiting the invention, which is defined by the appended claims and their legal equivalence.

What is claimed is:

1. A multi-function oxygen mask for the administration of a gas comprising, in combination:
   a mask body forming an internal cavity configured to cover a nose and a mouth of a patient, said mask body including an upper portion, a lower portion, a peripheral edge forming a sealing surface, a nasal chamber having an upper portion and a lower portion, an access aperture adjacent to said lower portion of said mask body, where the access aperture is symmetrically located about a centerline of the mask body, an upper sealing edge adjacent to said upper portion of said mask body and a gas delivery adapter aperture adjacent to said lower portion of said nasal chamber;
   a gas delivery adapter including a first end, a second end, an oxygen supply port adjacent to said first end and radially extending outward from said gas delivery adapter, a meter-dose inhaler port adjacent to said first end and radially extending outward from said gas delivery adapter and a nebulizer port adjacent to said second end, said first end of said gas delivery adapter coupled to said gas delivery adapter aperture, wherein said oxygen supply port has an external inlet portion, an outlet portion positioned within a volumetric space of said gas delivery adapter and a diverter member below and adjacent to said outlet portion, said diverter member extending from an inner surface of the gas delivery adapter towards a radial center of the gas delivery adapter and then towards said first end of the gas delivery adapter thereby forming a channel within the volumetric space of said gas delivery adapter and directing a flow from the outlet portion through the channel towards said first end of said gas delivery adapter; and
   a meter-dose inhaler insert within said meter-dose inhaler port, said meter-dose inhaler insert having a discharge port positioned within said volumetric space and configured to direct a flow towards said first end of said gas delivery adapter.

2. A multi-function oxygen mask as recited in claim 1, wherein the access aperture permits a secondary procedure to be administered without removal of the mask or disruption of oxygen therapy.

3. A multi-function oxygen mask as recited in claim 2, wherein the secondary procedure is selected from the group consisting of suctioning, oral care, feeding, and endoscopies.

4. A multi-function oxygen mask as recited in claim 1, wherein said upper sealing edge forms an angle β (Beta) with respect to a sealing surface such that a central inflection point is positioned substantially at a midpoint of a bridge of the nose of the patient, wherein said angle β (Beta) is between about 30 and about 75 degrees.

5. A multi-function oxygen mask as recited in claim 1, wherein the diverter member extends across less than an entire length of the gas delivery adapter.

6. A multi-function oxygen mask as recited in claim 1, wherein said upper sealing edge includes a right side and a left side that are each curved such that said upper portion of said mask body confirms to a facial structure of the patient.

7. A multi-function oxygen mask as recited in claim 1, further comprising a naso-gastric tube aperture formed through said mask body adjacent to said sealing surface, and a relief cut extending from said naso-gastric tube aperture through said sealing surface.

8. A method of fabricating a multi-function oxygen mask comprising the steps of:
   a) forming a mask body having an internal cavity configured to cover a nose and mouth of a patient, the mask body including an upper portion, a lower portion, a peripheral edge, a nasal chamber having an upper portion and a lower portion, an access aperture adjacent to the lower portion of the mask body, where the access aperture is symmetrically located about a centerline of the mask body, an upper sealing edge adjacent to the upper portion of the mask body and a gas delivery adapter aperture adjacent to the lower portion of the nasal chamber;
   b) coupling a first end of a gas delivery adapter to the gas delivery adapter aperture;
   c) providing an oxygen supply port adjacent to the first end of the gas delivery adapter, the oxygen supply port having an external inlet portion, an outlet portion positioned within a volumetric space of the gas delivery adapter;
   d) providing an L-shaped diverter member adjacent to the outlet portion, the diverter member extending towards a radial center of the gas delivery adapter and then towards said first end of the gas delivery adapter thereby forming a channel within the volumetric space of said gas delivery adapter and directing a flow only towards the first end of the gas delivery adapter;

e) providing a meter-dose inhaler port adjacent to said first end and radially extending outward from said gas delivery adapter; and f) inserting a meter-dose inhaler insert within the meter-dose inhaler port, the meter-dose inhaler insert having a discharge port positioned within the volumetric space and configured to direct a flow towards the first end of the gas delivery adapter.

9. A method of fabricating a multi-function oxygen mask as recited in claim 8, wherein the access aperture permits a secondary procedure to be administered without removal of the mask or disruption of oxygen therapy, where the secondary procedure is selected from the group consisting of suctioning, oral care, feeding, and endoscopies.

10. A method of fabricating a multi-function oxygen mask as recited in claim 8, wherein the channel within the volumetric space of the gas delivery adapter extends across less than the entire volumetric space.

11. A multi-function oxygen mask for the administration of a gas comprising:
   a mask body forming an internal cavity configured to cover a nose and a mouth of a patient, said mask body comprising:
      an upper portion, a lower portion, a peripheral edge, a sealing edge laterally extending outward from said peripheral edge, and an upper sealing edge formed adjacent to said upper portion of said mask body;
      a nasal chamber formed in said upper portion of said mask body; said nasal chamber including an upper portion, a lower portion and a gas delivery adapter aperture adjacent said lower portion of said nasal chamber;
      an access aperture formed through and adjacent to said lower portion of said mask body, said access aperture configured to permit access to the mouth of a patient;
   a gas delivery adapter having a general tubular structure, said gas delivery adapter comprising;
      a first end, an opposing second end, said first end of said gas delivery adapter coupled to said gas delivery adapter aperture;
      an oxygen supply port radially extending outward from said gas delivery adapter and adjacent to said first end of said gas delivery adapter, said oxygen supply port including an external inlet portion, an outlet portion positioned within a volumetric space of said gas delivery adapter and a diverter member adjacent to said outlet portion, said diverter member extending from an inner surface of the gas delivery adapter towards a radial center of the gas delivery adapter and then towards said first end of the gas delivery adapter thereby forming a channel within the volumetric space of said gas delivery adapter and directing a flow from the outlet portion through the channel towards said first end of said gas delivery adapter;
      a meter-dose inhaler port radially extending outward from said gas delivery adapter and a meter-dose inhaler insert within said meter-dose inhaler port, said meter-dose inhaler insert having a discharge port positioned within said volumetric space and configured to direct a flow towards said first end of said gas delivery adapter; and
      a nebulizer port extending longitudinally from said second end of said gas delivery adapter.

12. A multi-function oxygen mask as recited in claim 11, further comprising an oxygen supply port cover configured to seal said inlet portion of said oxygen supply port and a nebulizer port configured to seal said nebulizer port.

13. A multi-function oxygen mask as recited in claim 11, further comprising at least one naso-gastric tube aperture formed through said mask body and adjacent to said sealing edge and a relief cut extending from said naso-gastric tube aperture and through said sealing surface.

14. A multi-function oxygen mask as recited in claim 11, wherein said upper sealing edge forms an angle β (Beta) with respect to a sealing surface such that a central inflection point is positioned substantially at a midpoint of a bridge of the nose of the patient, wherein said angle β (Beta) is between about 30 and about 75 degrees.

15. A multi-function oxygen as recited in claim 11, wherein the access aperture permits a secondary procedure to be administered without removal of the mask or disruption of oxygen therapy, where the secondary procedure is selected from the group consisting of suctioning, oral care, feeding, and endoscopies.

16. A multi-function oxygen mask of claim 1, wherein the diverter member is integrally formed within the gas delivery adapter.

* * * * *